United States Patent [19]
Waters

[11] 3,944,471
[45] Mar. 16, 1976

[54] METHOD AND APPARATUS FOR DETECTING BIOLOGICAL ACTIVITY
[75] Inventor: John R. Waters, Towson, Md.
[73] Assignee: Johnston Laboratories, Inc., Cockeysville, Md.
[22] Filed: June 7, 1974
[21] Appl. No.: 477,452

[52] U.S. Cl............. 195/103.5 R; 195/54; 195/127; 195/139
[51] Int. Cl.²......................................... C12K 1/04
[58] Field of Search............. 195/103.5 R, 127, 139, 195/54

[56] References Cited
UNITED STATES PATENTS
3,676,679  7/1972  Waters.......................... 195/103.5 R

*Primary Examiner*—A. Louis Monacell
*Assistant Examiner*—Robert J. Warden

[57] ABSTRACT

A sample of materials such as blood, urine, spinal fluid, or the like to be tested for the presence of biological activity is placed into a first sterile container with a suitable growth medium which includes a $^{14}C$ carbon containing carbon source (such as $^{14}C$ substituted glucose) which is fermentable to produce gaseous $^{14}CO_2$. This first container is placed within a second container which also contains $CO_2$-absorbing material associated with a scintillation compound. The gaseous $^{14}CO_2$ generated in the first container diffuses into the outer container where it is absorbed and held in contact with the scintillation compound. The decay of $^{14}C$ will cause the scintillation compounds to emit light flashes which can be detected by a scintillation counter. Thus, the presence of $^{14}CO_2$ is detected in the same container in which the reaction is taking place.

34 Claims, 8 Drawing Figures

FIG. 1  FIG. 2  FIG. 3  FIG. 4  FIG. 5

METHOD AND APPARATUS FOR DETECTING BIOLOGICAL ACTIVITY

BACKGROUND OF THE INVENTION

The present invention relates to a method and apparatus for detecting $^{14}CO_2$ with a scintillation counter. The invention is especially useful for detecting the presence of biological activity and particularly for making rapid analyses of materials in which the presence of micro-organisms, or the like is suspected.

When, for example, bacteria are cultured in a suitable medium including a fermentable carbon source such as glucose, the source may be broken down to form $CO_2$ during the growth of the bacteria. If the growth medium is alkaline the $CO_2$ will generally be absorbed to form carbonates or bicarbonates. However, if the starting material is acidic (or slightly alkaline or neutral so that a slight amount of $CO_2$ absorption will convert the same to acidic conditions), gaseous $CO_2$ will be evolved into the atmosphere above the solution.

If the medium includes a carbon source prepared from radioactive carbon having an atomic weight of 14 ($^{14}C$) rather than normal carbon having atomic weight of 12, any $CO_2$ liberated will include radioactive $^{14}CO_2$. The radioactivity of the $^{14}CO_2$ which is the result of beta decay of the $^{14}C$, can be used to activate a scintillation compound, causing it to emit light flashes. A scintillation counter can be used to measure these emissions which will be generally related to the amount of $CO_2$ generated and thus can be used to measure the bacteria presence and growth in the medium.

Present methods for the detection and measurement of $^{14}CO_2$ (See, for example H. N. Wagner, "Principles of Nuclear Medicine" p. 796–97 published by W.B. Saunders, Philadelphia) absorb or trap the $^{14}CO_2$ in one operation and then transfer the absorber to a vial to which are added scintillating liquids. In a modification of this technique the absorber can be placed in a scintillation vial which is connected to the reaction flask by a conduit. These methods for determining bacteriological presence and growth by the radioactivity of the $CO_2$ evolved from the medium are slow and laborious, and possess considerable chance for error. It has also been proposed to position a filter paper coated with a $CO_2$ absorbing alkali salt and a scintillation compound between an open topped inner sample vial and an outer vial and measure the scintillations directly of this assembly. This system has a number of drawbacks. First the proposed inner vial is considerably smaller than the outer vial and therefore the amount of sample has to be small. Also the entire assembly has to be sterilized.

In hospital work, the early detection of bacteria and body fluids is of paramount importance. It has been a well recognized practice to place blood or urine specimens or the like in appropriate growth medium upon a Petri dish and make visual observations of bacteriological growth. While this method is also slow and laborious, it does facilitate the final identification of the bacteria. Manifestly, in each method, all samples, whether positive or negative for bacteria, had to be subjected to exhaustive procedures.

In many cases, a proper diagnosis and treatment of diseases would be facilitated if the absence of certain bacteria could be confirmed simply and quickly. Further, if such negative samples could be identified and discarded without extensive processing, much laboratory effort would be eliminated. The latter is also true if the presence of a certain species or at least of a certain group of bacteria could be established rapidly.

Another prior art method for determination of the presence of biological activity is described in U.S. Pat. No. 3,676,679, to Waters. In the system of this patent, the $^{14}CO_2$ evolved is withdrawn from the reaction vessel and analyzed in gaseous form in an ionization chamber for the presence of radioactivity.

SUMMARY OF THE INVENTION

It is an object of the present invention to provide a method and apparatus for the quick determination of the general presence or absence of bacteria in a given sample.

It is a further object of the invention to provide a method and apparatus for the determination of the general presence or absence of bacteria in a safe efficient manner with little chance for error.

It is also an object of the invention to provide sample container assembly that can be used directly in the detection and measurement of $^{14}CO_2$ with a standard liquid scintillation counter.

These and other advantages are achieved through the use of a novel analysis apparatus which comprises a first container adapted to receive a sample of a material together with a growth medium including a $^{14}C$ carbon containing carbon source which is fermentable to produce $^{14}CO_2$, said first container having removable sealing means operable to maintain a sterile environment within said first container; a second container adapted to receive said first container, whereby said first container occupies a substantial portion of the available space within said second container; detachable closure means operable to seal said second container; a paper absorbing means having associated therewith a scintillation compound, said paper absorbing means being disposed within the unoccupied portion of said second container.

The invention also includes an analysis apparatus including in addition to the above combination, means for exposing the combination to conditions conductive to the occurrence of normal metabolic processes and means for detecting light flashes emitted by the scintillation compound.

Further and in another aspect, the invention provides an analysis apparatus in which the paper absorbing means has been replaced by a transparent absorbing means.

The invention also provides a novel method for analyzing a material for the presence of biological activity which method comprises placing a sample of the material to be tested into a first container together with a growth medium including a $^{14}C$ carbon containing carbon source which is metabolizable or fermentable to produce gaseous $^{14}CO_2$; placing said first container within a second container, said second container having disposed therein a transparent $^{14}CO_2$-absorbing material associated with a scintillation compound; sealing this assembly by placing a cap over the opening of said second container; subjecting the assembly and thereby the medium with the sample therein to conditions conducive to the occurrence of normal metabolic processes for a period of time sufficient to cause production of $^{14}CO_2$ by the fermentation of said source; absorbing the gaseous $^{14}CO_2$ on said transparent absorbing material; and detecting the light emissions from said scintillation compound with a scintillation counter.

While the method and apparatus of the invention are not so limited, they are particularly adapted for the detection of medically significant bacteria.

DESCRIPTION OF THE PREFERRED EMBODIMENT

Figure 1:
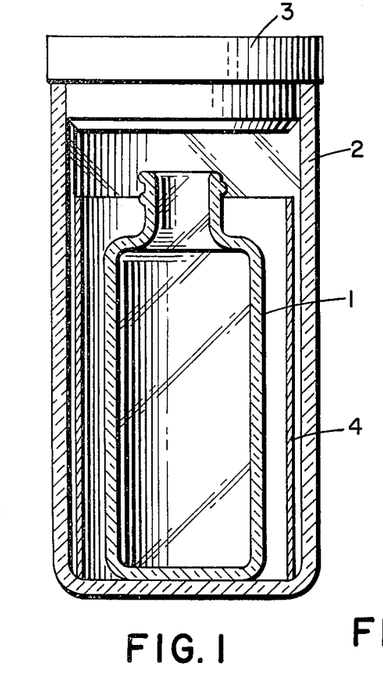
FIG. 1 represents an elevational view of the analysis apparatus of the present invention.

Reference is now made to the analysis apparatus of the present invention as shown in FIG. 1. This apparatus consists of an inner container 1, disposed within an outer container 2 which has a closure means 3. Also disposed within said outer container is the $CO_2$ absorbing means 4. The outer container is preferably a glass or plastic vial of the same overall dimensions (28 mm diameter by 60 mm long) as a standard scintillation counter vial. This allows the outer vial to be used without modification in scintillation counting instruments. For best results and high sensitivity, the outer vial is preferably made of a low-potassium glass which has the lowest background counting rate. In the preferred embodiment, this vial has sides which do not neck down (commonly called a shell vial) and has a plastic or rubger snap-cap 3 which makes the vial gas tight. This particular configuration allows for maximum volume in the inner vial which must slip inside the outer vial.

Figure 4:
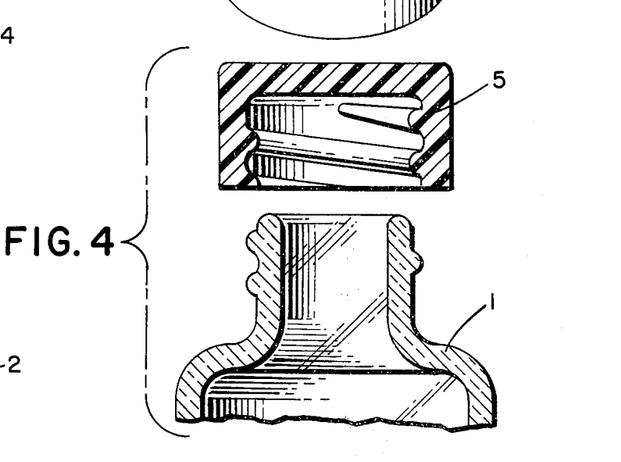
FIG. 4 represents one embodiment of the inner container sealing means.
Figure 5:
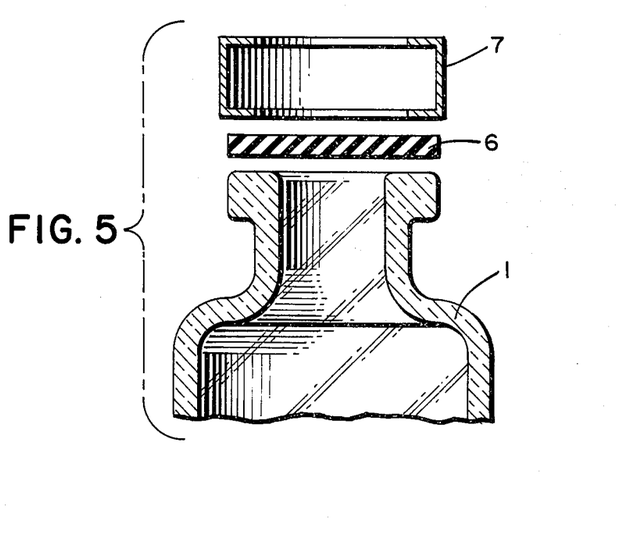
FIG. 5 represents an alternative inner container sealing means.

The inner vial 1 may be of glass or plastic and should have a diameter such that it fits easily inside the outer container. The inner vial should take up a substantial portion of the space in the outer vial as shown in FIG. 1, so as to maximize the sample size. Preferably the inner vial will have an outside diameter of about 22 to 24 mm and a height of about 50 mm. Its purpose is to contain the agents or chemicals that are reacting to produce the $^{14}CO_2$. When prepared in advance, it may be sealed with a screw cap 5 or by a standard serum vial closure 6/7 as shown in FIGS. 4 and 5. For some applications, it may be necessary to place a sterile cotton plug loosely in the neck of the inner vial to prevent debris from falling into the vial and contaminating it. Alternatively, a gas permeable water-repelling membrane, such as a micron-pore-size hydrophobic filter can be placed in or on the neck. Note, that only the inside of the inner vial needs to be sterile; the outside of the vial, the abosrber, the outer vial and the closure means need not be sterile.

Figure 2:
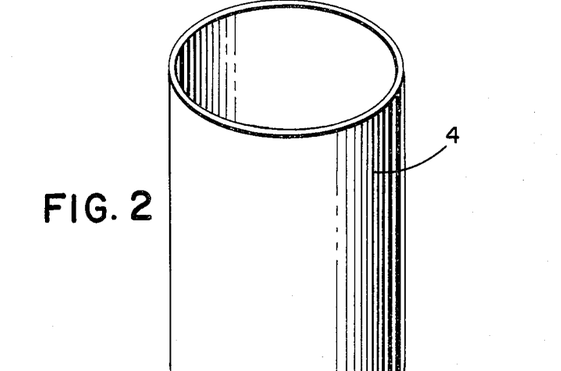
FIG. 2 represents one embodiment of the $CO_2$ absorbing means in the form of a removable cylinder.

The next component of the apparatus of the invention is the $^{14}CO_2$ absorbing means disposed within the outer container. The absorber may take many forms. In one embodiment, shown in FIG. 2, a cylinder of filter paper 4 which fits snuggly inside the outer vial is employed. This paper is treated with a concentrated liquid scintillation "cocktail" consisting of, for example, 100 grams of PPO (2,5-diphenyloxazole) and 1.25 grams of POPOP (p-bis(2-(5-phenyloxazoyl) benzene) in 1 liter of toluene. This mixture is commercially available as LIQUIFLUOR from New England Nuclear, Bost, Mass., and is well known in the art. About 0.2 to about 0.4 ml of this solution is trickled onto the paper so as to wet it uniformly. It is then dried by blowing warm air into it. Then about 0.1 to about 0.3 ml of 1 Normal NaOH (sodium hydroxide) is trickled onto the paper in the same way and the paper is redried.

Figure 6:
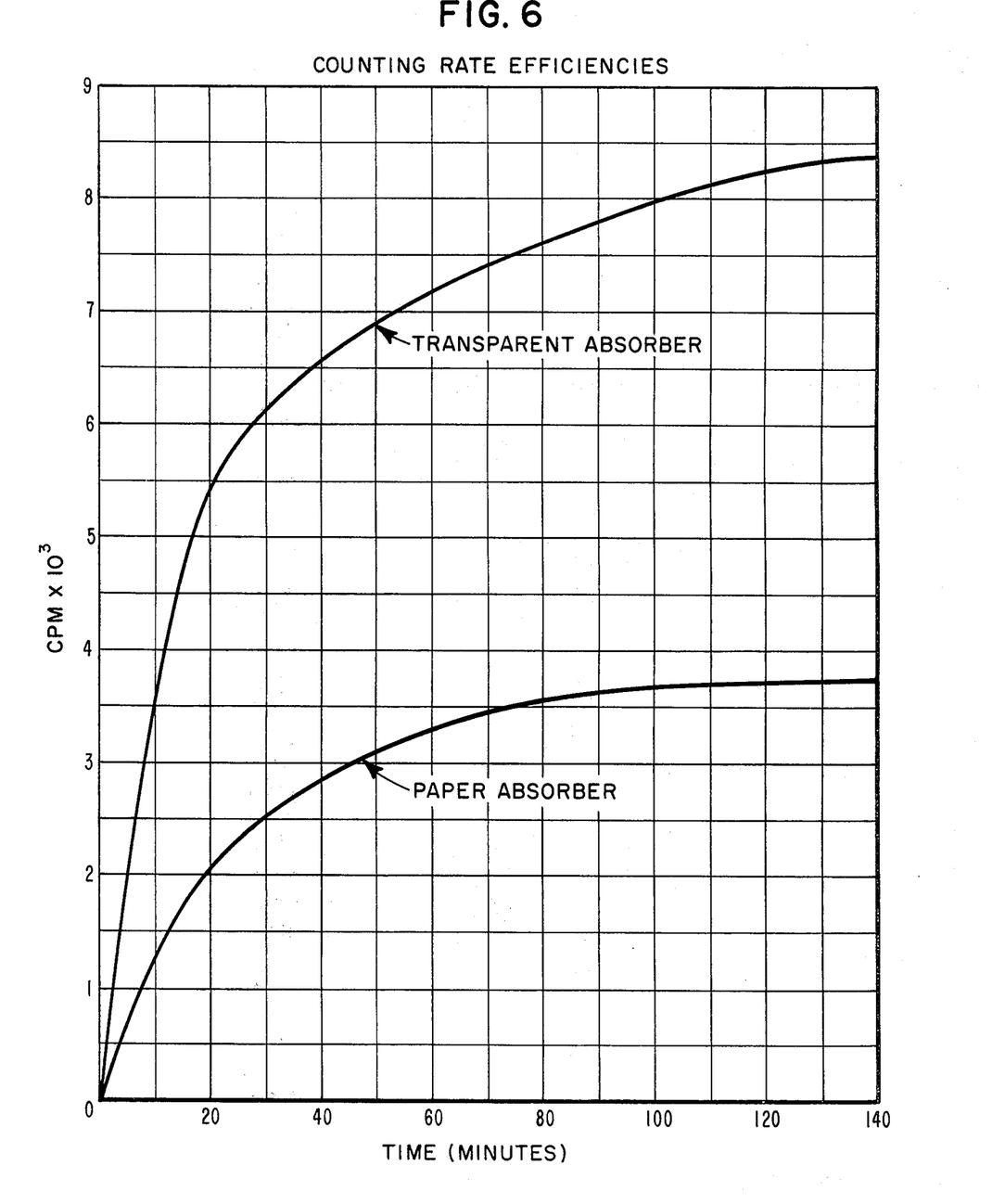
FIG. 6 is a graph of the counting efficiencies for the paper absorber and the transparent absorber.

Alternatively, the absorber may consist of any suitable configuration which will enable the $CO_2$ absorbing substance and the scintillating chemicals to be brought into close proximity, In one particularly advantageous embodiment, the absorber is formed from transparent material. When the absorber is transparent there is better optical coupling of the light emissions to the phototubes of the scintillation counter resulting in a higher detection efficiency. (See Example 1 and FIG. 6) The transparent absorber has other advantages over the paper absorber in that the paper becomes moist and sticky during use and is generally more difficult to handle than the transparent type absorbers. The paperless absorber method is also advantageous in that it allows the inner vial to be slightly larger in diameter, thus holding more of the solution to be tested.

Figure 3:
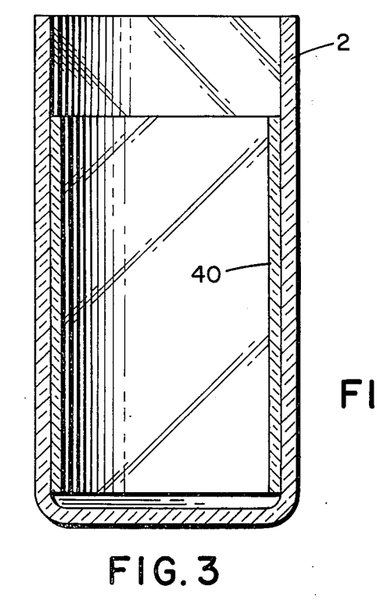
FIG. 3 represents an alternate embodiment of the $CO_2$ absorbing means in the form of a transparent coating on the inner surface of the outer container.

In one type of transparent absorber the inner wall of the outer vial can be used as the absorber to hold both the scintillating chemicals and an alkali absorber. The vial is cleaned and interior walls wetted with a scintillator solution similar to the one described above. The toluene solvent evaporates leaving a uniform, finely divided crystalline deposit 40 on the walls. The process is repeated with the alkali solution. Since the scintillating chemicals are not soluble in water they are not affected by the aqueous alkali solution. Alternatively, the alkali may be used to coat the walls first, followed, when dry, by coating with the scintillation solution. The transparent two-component absorber layer can also be coated on the outer surface of the inner vial. In addition to the wet coating method described above, a dry, finely ground mixed powder comprising an alkali and a scintillation compound can be applied to the vial surface with a thin film of adhesive.

The absorber/scintillator combination can also be effected by coating one of the components (e.g., the scintillation compound) on the inner surface of the outer vial and coating the other component (i.e., the alkali absorber on the outer surface of the inner vial. The outside diameter of the inner vial should be close enough to the inside diameter of the outer vial to allow for Beta activation, but it should not be so close as to cause abrasion of the coatings. Of course, it is possible to reverse the position of the two coatings. These separate coatings may be applied by the same methods employed to form the two-component coatings described above. For any type of coating method, it may be desirable to etch or sand blast the surface of the vial to give more effective surface area for holding the chemicals.

An alternative type of transparent absorber can consist of a thin shell of a solid plastic or glass scintillator material only a few thousandths of an inch thick. This shell can be coated with an alkali film on its surface to provide an absorber/scintillator. For any of the above absorber/scintillator combinations, it is possible to use other $CO_2$ absorbing compounds such as hyamine instead of the alkali.

The normal laboratory scintillation counter has the ability to handle from 100 to 500 or more scintillation vials, testing each one sequentially. Some instruments require that the vials and phototube detectors be operated in the range of 5° to 10° C. In other instruments the system operates at ambient room temperatures. In an application where it is desired to measure the $^{14}CO_2$ production from a metabolic process, it may be desireable to hold the vials at an elevated temperature, e.g., 35° C. The abmient temperature type of instrument can be easily modified for this application since the vial chamber may be heated while room temperature air is blown around the phototubes to cool them and prevent their performance from being degraded.

The detector apparatus embodying the principals and concepts of the invention as disclosed above is particularly useful, for example, in providing early detection of the general presence of most medically significant bacteria in material such as blood, urine, spinal fluid, water samples and the like. The presence of such bacteria is readily detected by measuring the light emissions from the scintillation materials which relates to the amount of $^{14}CO_2$ generated when material to be analyzed is placed in a growth medium including a $^{14}C$ carbon containing source (such as $^{14}C$ subsituted glucose) which is metabolized or fermented to produce $^{14}CO_2$ and the medium with the sample therein is therafter incubated. Manifestly, the presence of scintillation counts above the background level in the atmosphere above the growth medium is an indication of the presence of microorganisms in the original sample of the material. It should be noted that the term ferment as employed herein embraces metabolic processes generally.

In operation, a sample to be analyzed, such as blood, urine, or the like, is placed into a first sterile inner container 1 together with a growth medium which preferably includes $^{14}C$ glucose (all carbon atoms replaced by $^{14}C$). The inner vial can contain a general growth medium such as tryptic soy broth, to which is added one micro curie of $^{14}C$-U-glucose and, other $^{14}C$-labeled substrates. The inner vial should contain up to about 10 ml of liquid and it can be provided with a 20 mm standard serum vial closure. After dispensing the liquid into the vial, it is capped and sterilized by autoclaving. The serum vial closure may consist, as shown in FIG. 5, of a rubber septum 6 covered by an aluminum cap 7 which can be of the type that is easily removed by pulling a special tear-off tab. The inner vial is then placed in the outer vial 2, the sample inoculated into the inner vial, and the cap 3 put in place. After a short delay, any organisms present will grow rapidly followed by decrease in growth rate. The metabolism of the bacteria or other living organisms in the sample will generate $^{14}CO_2$ which will pass out of the liquid phase and diffuse into the outer container. The gas is then absorbed on the absorbent material and the decay of $^{14}C$ produces light flashes from the scintillation compounds absorbed thereon. These light flashes are detected by the phototubes in the scintillation counter and the counts are registered. Thus the presence of $^{14}CO_2$ is detected in the same container in which the reaction takes place.

This apparatus may be used, for example, to detect the presence of bacteria generally rather than to detect a given species. A growth medium which includes $^{14}C$ glucose is preferred and $^{14}C$ glucose constitutes a practical general purpose carbon source. However, it is to be understood that in some instances a given medium may be specific for a given species or at least for a known group and in those instances, the present invention may be utilized to detect the presence or absence of such species or members of such groups. Although glucose is the preferred medium because it is generally fermentable to form gaseous $CO_2$ by nearly all medically significant bacteria, it is to be appreciated that not all bacteria act on glucose to form gaseous $CO_2$. Sould a strain or class of bacteria be studied that does not produce $CO_2$ from glucose, some other carbohydrate such as xylose or maltose can be used to test for such microorganisms. The only necessity being that the carbohydrate include $^{14}C$ and that it is fermentable by the species or group of interest to form $^{14}CO_2$.

Standard nutrient mediums operable in this invention generally will contain water, a suitable $^{14}C$ substituted carbohydrate ($^{14}C$ glucose), a nitrogen source, calcium, magnesium, potassium, phosphate, sulfate and minor elements. The medium may also include a buffer for pH adjustment and maintanence. While, as stated above, $^{14}C$ glucose is the preferred carbon source, other $^{14}C$ substituted sugars as sucrose, fructose, xylose, maltose, lactose, and the like, as well as mixtures of such sugars, may be employed in the practice of this invention, generally for more specific determinations. The invention also contemplates the use of fermentation mediums containing $^{14}C$ carbon substituted carbohydrates generally including starches, dextrins, and the like as well as sugars. Other suitable $^{14}C$ containing carbon sources may be dipeptides such as phenylalanine, lysine, arginine, glycylglycine, or the like; glycerol, urea, or carboxylic acids such citric acid or the like; or mixtures of these with sugars or carbohydrates. Such radioactive materials are well known to those skilled in this art. As employed herein, the terms "sugar," "starch," and the like embrace not only such materials, per se, but their obvious equivalents such as, for example, molasses and the like. For maximum sensitivity, all of the carbon atoms in the carbon source are preferably replaced by $^{14}C$ carbon although this is not absolutely necessary so long as the $^{14}C$ is substituted in the correct position in the carbohydrate molecule so that it is liberated as $^{14}CO_2$. In this regard, it should be noted, as is well understood by those skilled in the art, that the $^{14}C$ cannot be substituted at random in the molecule, but its position must be carefully selected.

The carbohydrates are employed in the fermentation medium in amounts of at least 0.0001 percent by weight. Desirably the medium will contain from about 0.0003 percent to about 0.001 percent carbohydrate although fermentation mediums containing up to about 20 percent carbohydrate and above are operable. The $^{14}C$ activity supplied by the carbohydrate can be in the range of from less than 0.1 micro curie to about 10 micro curies or more per 10 ml of medium, although about 0.5 micro curies is preferred. It will be apparent that the precise proportion of carbohydrate employed in the medium will generally be a matter of choice.

The medium also may contain a standard nitrogen source, such as nitrates, nitrites, ammonia, urea or other assimilable nitrogen source either organic or inorganic. Preferably at least sufficient nitrogen is present to supply nitrogen for cell growth.

A variety of calcium, potassium, and magnesium salts may be employed in the fermentation medium including the chlorides, sulfates, phosphates, and the like. Similarly, phosphate and sulfate ions can be supplied as a variety of salts. While salts which supply both the desired anion and cation may be employed (e.g., potassium phosphate, magnesium sulfate) the selection is by no means so limited. Again, such materials are conventional in fermentaion mediums, and the selection of specific materials as well as their proportions is within the skill of the art.

The so-called "minor elements" are commonly understood to include maganese, iron, zinc, cobalt, and possibly others. Trace quantities thereof are preferred, in such quantities are commonly present in materials used in the preparation in the fermentation mediums.

Finally the medium may contain a buffer to maintain the pH in the desired range. Once more a variety of materials may be utilized. Potassium or ammonium phosphates often are employed to maintain the pH of fermentation media.

For effective fermentation for the majority of bacteria, the temperature of the medium at the sample therein is preferably maintained about 35° to about 39°C. Some organisms achieve optimum growth at a temperature of 20°C or lower while others may exhibit optimum growth at 45°C or higher. This invention may employ any temperature best suited in a given circumstance.

EXAMPLE 1

This example demonstrates the detection efficiencies of two embodiments of the invention as described above, that using a paper absorber and the embodiment which directly coats the absorber on the surface of the outer vial. In each case, 1 ml of strong nitric acid was placed in the inner vial assembled into the outer vial as shown in FIG. 1. Then 0.1 ml of a solution of $^{14}C$ sodium bicarbonate was injected by syringe through the plastic snap cap using a small needle (25 gauge). The hole in the cap was then sealed with a piece of tape. The acid converted all the $^{14}C$ in the bicarbonate to $^{14}CO_2$ which was absorbed and detected. The paper absorption method gave an equilibrium count rate of 3800 counts per minute while the paperless method gave a rate of 8350 cpm — a factor of 2.2 times better sensitivity. The results of this test are plotted in FIG. 6.

EXAMPLE 2

Figure 7:
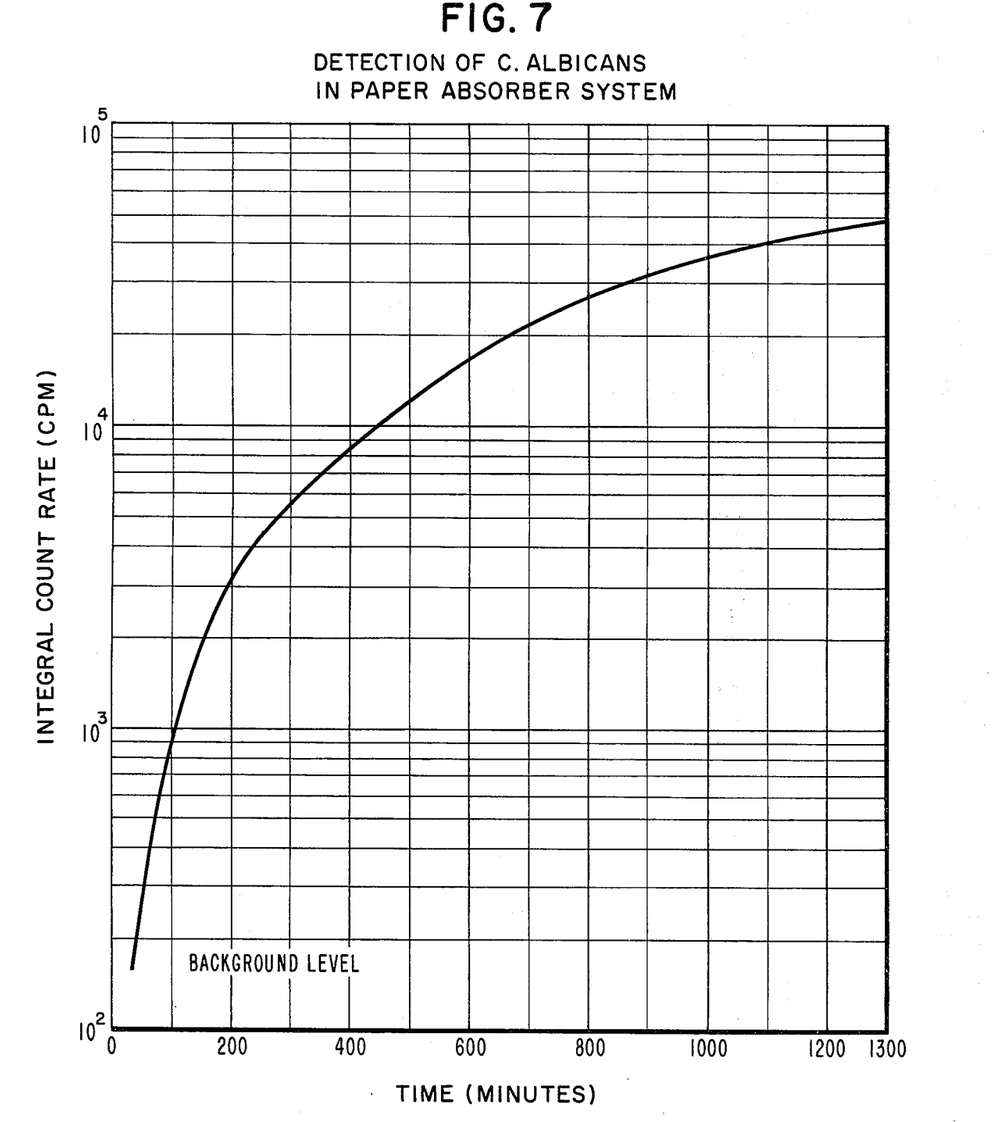
FIG. 7 represents a graph of the measured integral count rate during the detection of *C. Albicans* with 1 $\mu$Ci $^{14}$C-glucose in a paper absorber system.

As an example of the detection of living microorganisms, a heavy inoculum (0.5 ml) of an overnight growth of the yeast Candida albicans was inoculated into 2 ml of a culture medium (tryptic soy broth) containing 1 $\mu Ci$ of $^{14}C$ - glucose. This was placed in the inner vial, the paper absorber being used. The data in FIG. 7 shows the measured counting rates initially with 5 minute, and later with 20 minute, counting intervals. The rate rises rapidly from the background value from about 170 cpm and, within 100 minutes has increased by a factor of 10 and within 600 minutes has increased by a factor of 100. This data demonstrates the use of measurement of $^{14}CO_2$ produced by living microorganisms using the paper absorber apparatus of this invention.

EXAMPLE 3

Figure 8:
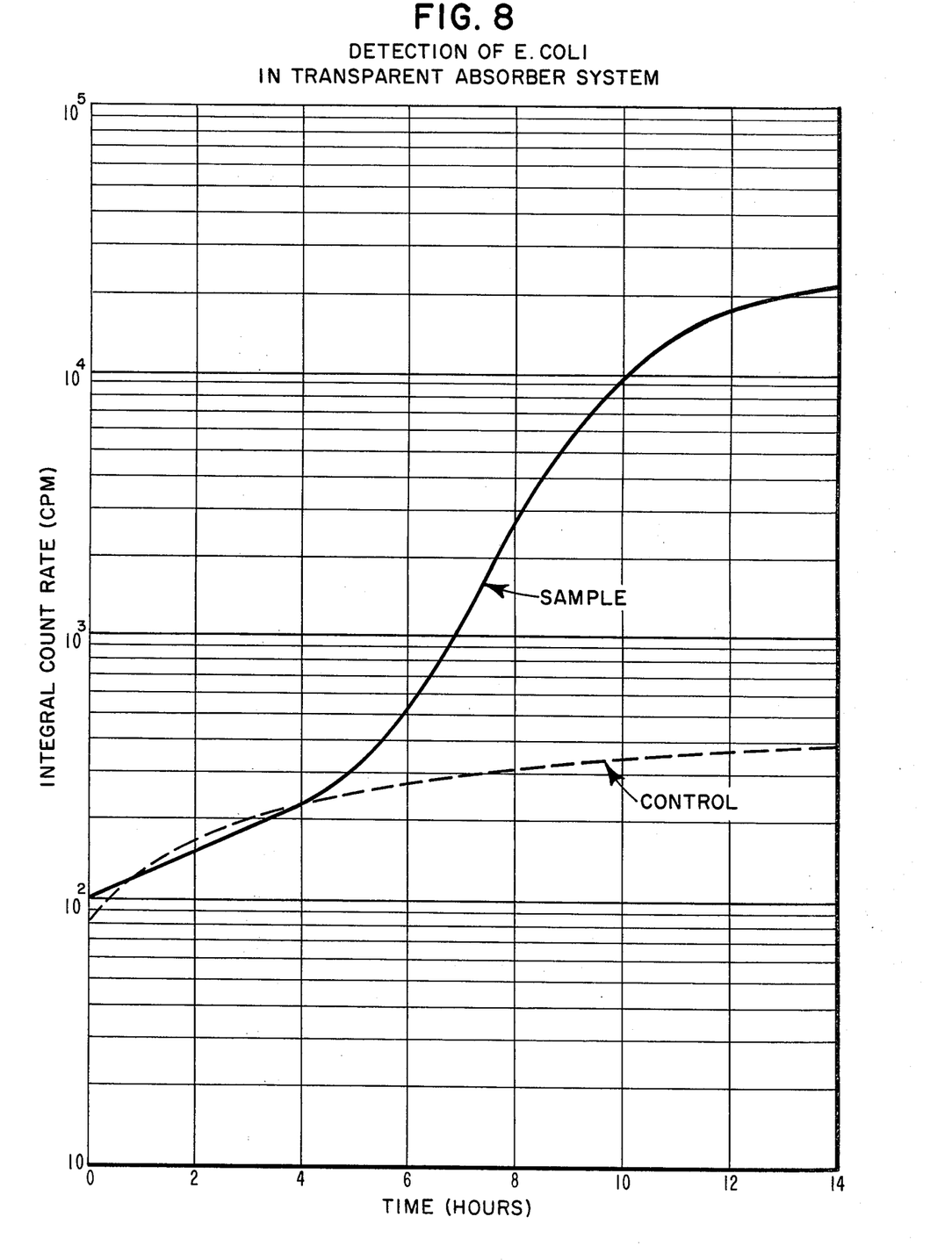
FIG. 8 represents a graph of the measured integral count rate during the detection of *E. coli* with 0.75 $\mu$Ci $^{14}$C-glucose in a system with transparaent absorber.

This example demonstrates the detection of living microorganisms by the transparent absorber technique. The absorber consisted of a mixed coating of an alkali and a scintillation compound on the inner surface of the outer vial. An inoculum (about 500 organisms) of an overnight growth of E. coli was inoculated into 5 ml of a culture medium (tryptic soy broth) containing about 0.75 $\eta Ci$ of $^{14}C$ - glucose. This was placed in the inner vial and the two vial assembly was placed in a standard liquid scintillation counter. A sterile control vial was also run. FIG. 8 shows the measured counting rates in this test. While there is a gradual rise in the control vial readings, there is a well defined point (when the readings get as high as 1000 cpm) where detection may be said to occur.

While the apparatus and method for its use have been described with respect to the detection of bacteria, the apparatus may be used to detect biological activity broadly including, inter alia other single cell organisms, enzymes and the like. Variations of the invention described herein with be apparent to those skilled in the art. It is intended, therefore, that the invention be limited only by the scope of the appended claims.

I claim:
1. An apparatus for the analysis of materials, said apparatus comprising:
    a first container adapted to receive a sample of said material together with a growth medium including a $^{14}C$ carbon containing carbon source which is fermentable to produce $^{14}CO_2$, said first container having removable sealing means operable to maintain a sterile environment within said first container;
    a second container adapted to receive said first container, whereby said first container occupies a substantial portion of the availbable space within said second container;
    closure means operable to seal said second container;
    a paper disposed within the unoccupied portion of said second container, said paper having deposited thereon a $^{14}CO_2$ absorbing compound and a scintillation compound, whereby the radioactivity of said absorbed $^{14}CO_2$ causes said scintillation compound to emit light flashes.
2. Th apparatus as set forth in claim 1 wherein said removable sealing means comprises a threaded cap.
3. The apparatus as set forth in claim 1 wherein said removable sealing means comprises a standard serum vial closure.
4. The apparatus as set forth in claim 1 wherein said removable sealing means comprises a gas permeable hydrophobic membrane.
5. The apparatus as set forth in claim 1 wherein said paper comprises a cylindrical sheet of absorbent paper impregnated with a $^{14}CO_2$ absorbing substance and a scintillation compound.
6. An apparatus for the analysis of materials, said apparatus comprising:
    a first container adapted to receive a sample of said material together with a growth medium including a $^{14}C$ carbon containing carbon source which is fermentable to produce $^{14}CO_2$, said first container having removable sealing means operable to mantain a sterile environment within said first container;

a second container adapted to receive said first container, whereby said first container occupies a substantial portion of the available space within said second container;
closure means operable to seal said second container;
means for exposing the medium and sample in said first and second containers to conditions conducive to the occurrence of normal metabolic processes;
a paper disposed within the occupied portion of said second container, said paper having deposited thereon a $^{14}CO_2$ absorbing compound and a scintillation compound, whereby the radioactivity of said $^{14}CO_2$ causes said scintillation compound to emit light flashes; and
means for detecting the light emissions from said scintillation compound.

7. The apparatus as set forth in claim 6 wherein said removable sealing means comprises a threaded cap.

8. The apparatus as set forth in claim 6 wherein said removable sealing means comprises a standard serum vial closure.

9. The apparatus as set forth in claim 6 wherein said removable sealing means comprises a gas permeable hydrophobic membrane.

10. The apparatus as set forth in claim 6 wherein said paper comprises a cylindrical sheet of absorbent paper impregnated with a $^{14}CO_2$ absorbing substance and a scintillation compound.

11. An apparatus for the analysis of materials, said apparatus comprising:
a first container adapted to receive a sample of said material together with a growth medium including a $^{14}C$ carbon containing carbon source which is fermentable to produce $^{14}CO_2$;
a second container adapted to receive said first container;
closure means adapted to seal said second container; and
transparent absorbing means for absorbing $^{14}CO_2$ and a scintillation compound disposed within said second container, said absorbing means being positioned to keep the absorbed $^{14}CO_2$ in close proximity with said scintillation compound whereby the radioactivity of said absorbed $^{14}CO_2$ causes said scintillation compound to emit light flashes.

12. The apparatus as set forth in claim II wherein said transparent absorbing means comprises a thin sheet of a solid transparent scintillating material coated with a $CO_2$ absorbing substance.

13. The apparatus as set forth in claim II wherein said transparent absorbing means comprises a layer containing a $CO_2$ absorbing substance and a scintillation compound, said layer being coated on the inner surface of the sides of said second container.

14. The apparatus as set forth in claim 11 wherein said transparent absorbing means comprises a layer containing a $CO_2$ absorbing substance and a scintillation compound, said layer being coated on the outer surface of the sides of said first container.

15. The apparatus as set forth in claim 11 wherein said transparent absorbing means comprises a first layer of a $^{14}CO_2$ absorbing substance and a second layer of a scintillation compound, said first layer being disposed on either the outer surface of said first container or the inner surface of said second container, and said second layer being disposed on the other of said surfaces.

16. The apparatus as set forth in claim II wherein said first container is adapted to receive a sealing means.

17. The apparatus as set forth in claim 16 wherein said sealing means comprises a threaded cap.

18. The apparatus as set forth in claim 16 wherein said sealing means comprises a standard serum vial closure.

19. The apparatus set forth in claim 16 wherein said sealing means comprises a gas permeable hydrophobic membrane.

20. An apparatus for the analysis of materials, said apparatus comprising:
a first container adapted to receive a sample of said material together with a growth medium including a $^{14}C$ carbon containing carbon source which is fermentable to produce $^{14}CO_2$;
a second container adapted to receive said first container;
closure means adapted to seal said second container;
means for exposing the medium and sample in said first and second containers to conditions conducive to the occurrence of normal metabolic processes;
transparent absorbing means for absorbing $^{14}CO_2$ and a scintillation compound disposed within said second container, said absorbing means being positioned to keep the absorbed $^{14}CO_2$ in close proximity with said scintillation compound whereby the radiocactivity of said absorbed $^{14}CO_2$ causes said scintillation compound to emit light flashes; and
means for detecting the light emissions from said scintillation compound.

21. The apparatus as set forth in claim 20 wherein said transparent absorbing means comprises a thin sheet of a solid transparent scintillating material coated with a $CO_2$ absorbing substance.

22. The apparatus as set forth in claim 20 wherein said transparent absorbing means comprises a layer containing a $CO_2$ absorbing substance and a scintillation compound, said layer being coated on the inner surface of the sides of said second container.

23. The apparatus as set forth in claim 20 wherein said transparent absorbing means comprises a layer containing a $CO_2$ absorbing substance and a scintillation compound, said layer being coated on the outer surface of the sides of said first container.

24. The apparatus as set forth in claim 20 wherein said transparent absorbing means comprises a first layer of a $^{14}CO_2$ absorbing substance and a second layer of a scintillation compound, said first layer being disposed on either the outer surface of said first container or the inner surface of said second container, and said second layer being disposed on the other of said surfaces.

25. The apparatus as set forth in claim 20 wherein said first container is adapted to receive a sealing means.

26. The apparatus as set forth in claim 25 wherein said sealing means comprises a threaded cap.

27. The apparatus as set forth in claim 25 wherein said sealing means comprises a standard serum vial closure.

28. The apparatus as set forth in claim 25 wherein said sealing means comprises a gas permeable hydrophobic membrane.

29. A method for analyzing a material for the presence of biological activity, said method comprising:
placing a sample of said material into a first container together with a growth medium including a $^{14}C$ carbon containing carbon source which is fermentable to produce $^{14}CO_2$;

placing said first container into a second container, said second container also having disposed therein a transparent $^{14}CO_2$ absrobing absorbing in close proximity with a scintillation compound;

sealing the thus formed assembly by placing a cap over the opening of said second container;

subjecting the assembly and thereby the medium and the sample therein to conditions conducive to the occurrence of normal metabolic processes for a period of time sufficient to cause production of $^{14}CO_2$ by the fermentation of said source;

thus absorbing the gaseous $^{14}CO_2$ on said transparent absorbing material; and detecting the light emissions from said scintillation compound with a scintillation counter.

30. The method of claim 29 wherein said source comprises $^{14}C$ substituted glucose.

31. The method of claim 29 wherein said transparent absorbing material comprises a thin sheet of solid transparent scintillation material coated with a $CO_2$ absorbing substance.

32. The method of claim 29 wherein said transparent absorbing material comprises a layer containing a $CO_2$ absorbing substance and a scintillation compound, said layer being coated on the inner surface of the sides of said second container.

33. The method of claim 29 wherein said transparent absorbing material comprises a layer containing a $CO_2$ absorbing substance and a scintillation compound, said layer being coated on the outer surface of the sides of said first container.

34. The method of claim 29 wherein said transparent absorbing material comprises a first layer of a $^{14}CO_2$ absorbing substance and a second layer of a scintillation compound, said first layer being disposed on either the outer surface of said first container or the inner surface of said second container, and said second layer being disposed on the other of said surface.

* * * * *

UNITED STATES PATENT OFFICE
CERTIFICATE OF CORRECTION

Patent No. 3,944,471          Dated March 16, 1976

Inventor(s) John R. Waters

It is certified that error appears in the above-identified patent and that said Letters Patent are hereby corrected as shown below:

Col. 1, line 33:     "bacteria" should read -- bacterial --

Col. 2, line 42:     "conductive" should read -- conducive --

Col. 3, line 43:     "rubger" should read -- rubber --

Col. 3, line 64:     "abosrber" should read -- absorber --

Col. 8, line 10:     "0.75$\eta$Ci" should read -- 0.75 $\mu$Ci --

Claim 2, line 1:     "Th" should read -- The --

Claim 19, line 1:    The word "as" was omitted and should be added after the word "apparatus"

Claim 29, line 9,    The word "absrobing" should be deleted. The word "material" was omitted and should be inserted after the word "absorbing"

Signed and Sealed this

Ninth Day of November 1976

[SEAL]

Attest:

RUTH C. MASON
Attesting Officer

C. MARSHALL DANN
Commissioner of Patents and Trademarks